(12) United States Patent
Felder

(10) Patent No.: US 11,186,629 B2
(45) Date of Patent: Nov. 30, 2021

(54) TREATMENT METHOD FOR COCKAYNE SYNDROME

(71) Applicant: Marv Enterprises, LLC, Hermitage, PA (US)

(72) Inventor: Mitchell S. Felder, Hermitage, PA (US)

(73) Assignee: HALBERD CORPORATION, Jackson Center, PA (US)

( * ) Notice: Subject to any disclaimer, the term of this patent is extended or adjusted under 35 U.S.C. 154(b) by 0 days.

(21) Appl. No.: 16/782,486

(22) Filed: Feb. 5, 2020

(65) Prior Publication Data

US 2020/0291101 A1 Sep. 17, 2020

Related U.S. Application Data

(63) Continuation-in-part of application No. 15/933,619, filed on Mar. 23, 2018, now abandoned.

(60) Provisional application No. 62/488,649, filed on Apr. 21, 2017.

(51) Int. Cl.
*C07K 16/18* (2006.01)
*A61M 1/36* (2006.01)

(52) U.S. Cl.
CPC .......... *C07K 16/18* (2013.01); *A61M 1/362* (2014.02); *C07K 2317/76* (2013.01)

(58) Field of Classification Search
None
See application file for complete search history.

(56) References Cited

U.S. PATENT DOCUMENTS

| 8,758,287 | B2 | 6/2014 | Felder | |
|---|---|---|---|---|
| 8,865,733 | B2 | 10/2014 | Felder | |
| 9,216,386 | B2 | 12/2015 | Felder | |
| 2012/0000838 | A1* | 1/2012 | Felder | B01D 61/28 210/175 |
| 2018/0078641 | A1 | 3/2018 | Felder et al. | |

OTHER PUBLICATIONS

NCBI for DAP protein, downloaded from https://www.ncbi.nlm.nih.gov/gene/1611, on Jan. 30, 2021 (Year: 2021).*
Cruse et al., Illustrated Dict. of Immunology, 2nd ed., CRC Press, 2003, p. 46 (Year: 2003).*
Mateu et al. (Mateu MG, et. al. Eur J Immunol. Jun. 1992;22(6):1385-9.) (Year: 1992).*
Greenspan et al. (Greenspan NS, Di Cera E. Defining epitopes: It's not as easy as it seems. Nat Biotechnol. Oct. 1999;17(10):936-7. (Year: 1999).*
Potocnakova et al (J Immunol Res. (2016);2016:6760830; pp. 1-11) (Year: 2016).*
Millipore Sigma page on Antibodies (downloaded from https://www.sigmaaldrich.com/technical-documents/articles/biology/antigens-epitopes-antibodies.html on Jan. 30, 2021) (Year: 2021).*
Vajdos et al. (J Mol Biol. Jul. 5, 2002;320(2):415-28 (Year: 2002).*
Thermofisher Scientific (downloaded from https://www.thermofisher.com/us/en/home/life-science/antibodies/primary-antibodies/antibodies-applications/antibodies-immunoprecipitation.html#:~:text=Whether%20it%20will%20work%20in,recognized%20in%20its%20native%20state on Jan. 30, 2021) (Year: 2021).*
Kubota et al (Pediatrics International (2015) 57,339-347 (Year: 2015).*

* cited by examiner

*Primary Examiner* — Brian Gangle
*Assistant Examiner* — Andrea K McCollum
(74) *Attorney, Agent, or Firm* — Ference & Associates LLC

(57) ABSTRACT

Disclosed is a method for treating of Cockayne Syndrome (CS). Specifically, the invention pertains to a method for the extracorporeal treatment of a body fluid by removing the body fluid from a living body diseased with CS, and applying a targeted antibody either a mammalian target of rapamycin (mTOR) antigen or a death-associated protein 1 (DAP1) in a bodily fluid such as blood, creating an antibody-antigen complex, removing antibody-antigen complex from the bodily fluid, and returning the purified bodily fluid to the CS patient.

3 Claims, No Drawings
Specification includes a Sequence Listing.

SEQUENCE LISTING

```
<160> NUMBER OF SEQ ID NOS: 1

<210> SEQ ID NO 1
<211> LENGTH: 77
<212> TYPE: PRT
<213> ORGANISM: homo sapien

<400> SEQUENCE: 1

Gln Phe Arg Pro Asn Pro Thr Leu Leu Gly Asn Leu Arg Gln Asn Gln
1               5                   10                  15

Val Leu Cys Pro Leu Pro Tyr Ile Ser Ile Phe Lys Thr Arg Asn Ser
            20                  25                  30

Ser Ser Pro Asn Leu Val Tyr Gly Glu Ser Gly Trp Met Ser Phe Glu
```

-continued

```
            35                  40                  45
Asp His Cys Ala Pro Arg Gly Ala Ile Ser Arg Ile Cys Gln Asp Pro
    50                  55                  60

Arg Lys Ile Leu Ala Leu Val Leu Phe Gln Gln Ser Pro
65                  70                  75
```

TREATMENT METHOD FOR COCKAYNE SYNDROME

This application is a Continuation in part of U.S. Non-provisional application Ser. No. 15/933,619 filed on Mar. 23, 2018 which in turn claims priority to U. S. Provisional Application Ser. No. 62/488,649 filed on Apr. 21, 2017, the contents of which are fully incorporated in this disclosure.

FIELD OF THE INVENTION

This disclosure relates to a treatment for slowing and reversing the disease processes relating to Cockayne Syndrome utilizing an extracorporeal methodology to achieve this purpose.

BACKGROUND OF THE INVENTION

Cockayne syndrome (CS) is an inherited autosomal recessive trait where both parents are obligate carriers of an abnormal gene (ERCC6 or ERCC8). The incidence of CS is estimated at approximately 1 per 2.7 per million births, although according to recent studies, CS is likely under diagnosed. Children with CS typically experience abnormalities that aid in the differential diagnosis of the disease. These abnormalities include congenital anomalies of the face, limbs, heart, viscera, metabolic and neurologic crises, hematologic issues and a variety of malignancies. CS spans a phenotypic spectrum that includes CS type I, the "classic" or "moderate" form.

CS type I (moderate CS) is characterized by normal prenatal growth with the onset of growth and developmental abnormalities in the first two years. By the time the disease has become fully manifest, height, weight, and head circumference are far below the norm expected in a healthy child. Progressive impairment of vision, hearing, and central and peripheral nervous system function leads to severe disability; death typically occurs in the first or second decade. A recent study demonstrated that more than 30 proteins are involved in the CS-B interactome and may be involved in the pleiotropic functions of CS-B. CS-B is known to be involved in DNA break repair and checkpoint regulation.

Classic CS is diagnosed by clinical findings including postnatal growth failure and progressive neurologic dysfunction along with other minor criteria. Molecular genetic testing or a specific DNA repair assay on fibroblasts can confirm the diagnosis. The two primary genes in which mutations are known to cause CS are ERCC6, which codes for the CS-B protein (65%) of and ERCC8, which codes for the CS-A protein (35%). Most variants are identified by sequence analysis of ERCC6 and ERCC8. Both genes are members of the family of excision-repair cross complementation group. Mutation in either of these genes results in deficits in DNA checkpoint regulation and in DNA repair mechanisms. Recent evidence also suggests a role for CS-A and CS-B in response to oxidative stress. Currently, the only drug therapy for patients suffering from CS is Prodarsan. Prodarsan is a drug (10% D-mannitol) that was provided orphan status and has been evaluated for its ability to reduce the accumulation of DNA damage.

CS-B is involved in DNA repair and transcription. CS-B is present in mitochondria, where it associates with mitochondrial DNA. Mitochondrial content is increased in CS-B deficient cells whereas autophagy is down-regulated. CS-B-deficient cells show increased free radial production and accumulation of damaged mitochondria.

The mammalian target of rapamycin (mTOR) pathway is a highly conserved signal transduction axis involved in many cellular processes, such as cell growth, survival, transcription, translation, apoptosis, metabolism, motility and autophagy. Inhibition of mTOR is found to extend the lifespan in diverse animal models. Death-associated protein 1 (DAP1) is a novel substrate of mTOR that negatively regulates autophagy.

Treatment of CS-B deficient cells with autophagic stimulators such as rapamycin which is known to inhibit mTOR reverses the bioenergetic phenotype of CS-B-deficient cells which suggests that removing mTOR and its substrate DAP-1 as treatment options for patient's with CS accelerated aging phenotype.

SUMMARY OF THE INVENTION

Disclosed is a method of extracorporeal treating a Cockayne Syndrome patient's body fluid by removing mTOR and/or DAP-1 from a patient's blood or cerebral spinal fluid (CSF) U.S. Ser. Nos. 13/128,870, 13/128,177, 13/254,855, US 61/612,474, and US 61/644,292 are hereby incorporated by reference.

DETAILED DESCRIPTION OF THE INVENTION

The method disclosed comprises treating a patient's body fluid extracorporeally with an antibody or multiple antibodies designed to react and precipitate out targeted antigens of either death-associated protein 1 (DAP1) and/or mammalian target of rapamycin (mTOR) proteins, removal of those proteins from the patient's bodily fluid and returning the cleansed bodily fluid back to the patient. As a non-limiting example, treatment of a patient's blood may comprise removing 25 mL to 500 mL of blood from a patient using a catheter, and then applying the treatment to the blood before returning it to the patient via the same catheter. Immunoprecipitation is utilized to achieve the desired treatment, the removal of the mTOR and/or DAP1 proteins. Immunoprecipitation is used to isolate and concentrate the targeted antigens of DAP1 and/or mTOR proteins from a heterogeneous body fluid containing many thousands of different proteins. Purification and collection of the targeted proteins is performed by using antibodies against targeted antigens specific for either or both of the DAP1 and/or mTOR proteins. As a non-limiting example, a monoclonal antibody against a targeted antigen is immobilized onto magnetic beads, and then mixed with the CS patient's bodily fluid containing mTOR and DAP1. Gentle agitation of the bodily fluid allows the target antigen to bind to the immobilized antibody forming antibody/antigen complexes. Non-limiting examples of magnetic beads that could be used are Dynabeads® or Pierce® magnetic beads. High powered magnets are used to localize the magnetic beads to the side of the treatment chamber to enable cell lysate aspiration. Non-limiting examples of such chambers can be found in U. S. application Ser. No. 13/254,855. Instrumentation may be used to automate the magnetic bead and immunoprecipitation procedures.

There are numerous commercial antibodies that will achieve the method of treatment of a patient's bodily fluid by immunoprecipitation. For example, anti-DAP1 antibody ab244432 from abcam. This is a polyclonal antibody that reacts with a recombinant fragment corresponding to Human DAP1 aa 86-162: SEQ ID NO: 1. Another antibody from abcam, anti-DAP1 ab32056, is a monoclonal antibody that reacts with Human DAP1 aa 50-150 (C terminal). The exact sequence is proprietary. Examples for anti-mTOR antibodies include ab2732 and ab32028 from abcam. Ab2732 is a polyclonal antibody that reacts with Human mTOR aa 200-500 (exact sequence is proprietary) and ab32028 is a monoclonal antibody that reacts with Human mTOR aa 2400-2500 (C Terminal, exact sequence is proprietary). Any antibody equivalent to the above that is capable of immunoprecipitation is contemplated by this disclosure.

Any of above described targeted antibodies or their equivalents may also be utilized in a dialysis method of removal. The patient's blood is removed, exposed to an appropriate antibody (anti-mTOR or anti-DAPI) and removal of the resulting antibody/antigen complex is performed by dialysis. Said antibodies may be conjugated with a moiety such as albumin. Conjugation with such a moiety permits efficacious dialysis for the removal of the targeted antibody/antigen complex. Though dialysis with antibody/antigen complex alone may be sufficient for removal by dialysis or with system compatible with dialysis or with equipment used synergistically with dialysis. Removal of the complex can be done using a dialysis machine as known to those with skill in the art. Removal also can be done using a molecular filter which may be compatible and/or synergistic with dialysis equipment. One such system consists of elements from extracorporeal renal replacement techniques such as hemodialysis, ultrafiltration, and adsorption. This system is an extracorporeal hemodialysis system composed of three different circuits: blood, albumin and low-flux dialysis. The blood circuit uses a double lumen catheter (venovenous access) and a conventional hemodialysis device (blood roller pump and continuous venovenous hemfiltration monitor) to pump the patient's blood into a biocompatible polysulfone (non-albumin permeable) high-flux dialyzer. The blood flow rate will be 150-250 ml/min depending on the clinical status of the patient. Then blood will be passed on to the albumin circuit containing 20% serum albumin, where blood is dialyzed, allowing for the detoxification of both water-soluble and protein-bound toxins, by means of the presence of albumin in the dialysate (albumin dialysis). The albumin dialysate is then regenerated in a close loop by passing through the fibres of the low-flux filter, to clear water-soluble toxins and provide electrolyte/acid-base balance, by a standard dialysis fluid. The albumin dialysate passes through two different adsorption columns; protein-bound substances are removed by one column containing activated charcoal, and anionic substances are removed a second column filled with cholestyramine, an on-exchange resin. Heparin is used as an anti-coagulant. The activated clotting time, utilizing heparin is maintained between 160-190 seconds. The albumin solution is then ready to initiate another detoxifying cycle of the patient's blood that can be sustained until both adsorption columns are saturated, eliminating the need to continuously infuse albumin into the system during treatment.

After the body fluid had passed through a removal process, a portion the body fluid can be tested to identify any remaining unbound DAP1 and/or mTOR or antibody/antigen complexes before returning the body fluid to the patient. Body fluids with unacceptably large concentrations of unbound DAP1 and/or mTOR, or antibody/antigen complexes remaining can then be put back through the removal process(es) before returning the body fluid to the patient.

DAP1 and/or mTOR can be identified using standard enzyme-linked immunosorbent assay (ELISA) methodology. ELISA is a biochemical technique, which allows for the detection of an antigen in a sample. In ELISA an antigen is affixed to a surface, and then an antibody is utilized for binding to the antigen. The antibody is linked to an enzyme, which enables a color change in the substrate.

Other strategies may be used to validate the level of unbound DAP1 and/or mTOR or antibody/antigen complexes in the body fluid: Western blotting technology, UV/vis spectroscopy, mass spectroscopy, chromatography, and surface plasmon spectroscopy.

Another alternative methodology for identifying unbound DAP1 and/or mTOR or antibody/antigen complexes remaining in the body fluid would be to utilize molecular weight cut-off filtration. Molecular weight cut-off filtration refers to the molecular weight at which at least 80% of the target antigen(s) is prohibited from membrane diffusion.

After the removal of the complexes, the cleansed bodily fluid can then be returned to the patient. Rapamycin, as a therapeutic agent may be added into the bodily fluid before returning to the patient to further enhance the inhibition of mTOR/DAP1 remaining in the body after harmful DAP1 and/or mTOR proteins are removed from the bodily fluid.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

A Sequence Listing is submitted with this application and is incorporated by reference into this application. The Sequence Listing is in an ASCII text file entitled SEQ CS app created on Mar. 12, 2020 and the size of the text file 1,000 bytes.

The invention claimed is:

1. A method of treating a Cockayne Syndrome (CS) patient comprising:
   removing bodily fluid from said CS patient;
   exposing the bodily fluid to magnetic beads comprising immobilized antibodies; said immobilized antibodies being reactive against a specific antigen, said antigen being death-associated protein 1 (DAP 1); said immobilized antibodies and said antigen forming antibody/antigen complexes, thereby immunoprecipitating said antigen out of the bodily fluid;
   removing said magnetic beads from the body fluid; and
   returning the bodily fluid to the CS patient.

2. A method of treating a Cockayne Syndrome (CS) patient comprising:
   removing blood from said CS patient;
   exposing the blood to antibodies; said antibodies being reactive against a specific antigen, said antigen being death-associated protein 1 (DAP 1); said antibodies and said antigen forming antibody/antigen complexes in the blood;
   removing the antibody/antigen complexes formed in the blood using dialysis, and
   returning the blood to the CS patient.

3. A method of treating a Cockayne Syndrome (CS) patient comprising:
   removing blood from said CS patient;
   exposing the blood to antibodies; said antibodies being reactive against a specific antigen, said antigen being death-associated protein 1 (DAP 1); said antibodies and said antigen forming antibody/antigen complexes in the blood;
   removing the antibody/antigen complexes formed in the blood using an extracorporeal hemodialysis system, said extracorporeal hemodialysis system being composed of three different circuits: blood, albumin, and low-flux dialysis; and
   returning the blood to the CS patient.

* * * * *